United States Patent [19]

Schrock

[11] Patent Number: 4,681,956

[45] Date of Patent: Jul. 21, 1987

[54] CATALYST COMPOSITION FOR EFFECTING METATHESIS OF OLEFINS

[75] Inventor: Richard R. Schrock, Winchester, Mass.

[73] Assignee: Massachusetts Institute of Technology, Cambridge, Mass.

[21] Appl. No.: 780,049

[22] Filed: Sep. 25, 1985

[51] Int. Cl.$^4$ ............................................. C07F 11/00
[52] U.S. Cl. ..................................... 556/12; 502/155; 556/9; 556/58; 585/645
[58] Field of Search ....................... 502/155; 556/9, 12, 556/58

[56] References Cited

U.S. PATENT DOCUMENTS

| | | | |
|---|---|---|---|
| 3,450,797 | 6/1969 | Schafer et al. | 502/155 X |
| 4,247,417 | 1/1981 | Banasiak | 502/155 |
| 4,427,595 | 1/1984 | Schrock | 556/58 X |

FOREIGN PATENT DOCUMENTS 1601567 8/1970 France ................................ 502/155

Primary Examiner—Patrick P. Garvin
Attorney, Agent, or Firm—Jake Maslow

[57] ABSTRACT

Compounds of the formula:

$$M(NR^1)(OR^2)_2(CHR^3)$$

wherein
M is molybdenum or tungsten;
$R^1$ and $R^2$ are alkyl, aryl, aralkyl or halogen-substituted derivatives or silicon-containing analogs thereof;
$R^3$ is an alkyl, aryl, aralkyl or any substituent that results from the initial reaction between the M=$CHR^3$ complex and the olefin(s) that is(are) being metathesized; alkyl has 1–20 carbons, aryl has 6–20 carbons and aralkyl h as 7–20 carbons.

These compounds are catalysts for the metathesis of ordinary olefins (hydrocarbons) and especially functionalized olefins in the homogeneous phase.

7 Claims, No Drawings

CATALYST COMPOSITION FOR EFFECTING METATHESIS OF OLEFINS

The Government has rights in this invention pursuant to Grant No. CHE 84-02892 awarded by the National Science Foundation.

BACKGROUND OF THE INVENTION

The invention relates to homogeneous catalysts for the metathesis of olefins, including functionalized olefins, a process that is defined as the redistribution of alkylidene moieties in a mixture of olefins to give all possible olefins. The simplest example is $$2R'CH=CHR \rightleftharpoons R'CH=CHR' + RCH=CHR$$

The reaction proceeds by addition of an olefin to a metal-carbon double bond (M=CHR, a metal-alkylidene complex) to give a metal-lacyclobutane ring, which then releases an olefin to reform a metal-alkylidene complex.

Prior to this invention, there has been no report of a well-characterized tungsten or molybdenum catalyst for the metathesis of functionalized olefins. The tungsten catalyst system that is known consists of $WCl_6$ activated by a stoichiometric quantity of a tetraalkyltin reagent at 110° C. (J. C. Mol *J. Molec. Catal.* 15 (1982) 35; J. C. Mol *Chem. Tech.* 13 (1983) 250; R. H. A. Bosma, G. C. N. Van den Aardweg and J. C. Mol *J. Organometal. Chem.* 255 (1983) 159). Variations are known such as the catalyst system consisting of $WOCl_4$ activated by $Ti(\eta^5-C_5H_5)_2(CH_3)_2$ (J. Tsuji and S. Hashiguchi *Tet. Lett.* 21 (1980) 2955), $WCl_6$ activated with $BEt_3$ (R. Nakamura, S. Fukuhara, S. Matsumoto and K. Komatsu *(Chem. Lett.* (1976) 253; R. Nakamura, S. Matsumoto and E. Echigoya *Chem. Lett.* (1976) 1019), $Mo(OEt)_2Cl_3$ activated by $BEt_3$ (Nakamura) and $WCl_6$ activated by $Al_2Me_3Cl_3$ (Nakamura).

A second catalyst system that appears to be more active and long-lasting than tungsten-based systems is a heterogeneous catalyst prepared by depositing $Re_2O_7$ on silica or alumina and activating it with tetraalkyltin reagents (see articles by Mol above). It is active at room temperature.

A typical olefin of interest for testing catalysts is an ester of oleic acid, owing to the great abundance of oleic acid in natural oils such as olive oil (oleic acid=-cis—$CH_3(CH_2)_7CH=CH(CH_2)_7CO_2H$). The characteristic of all catalyst systems known so far is that they are relatively slow, sometimes unselective, sometimes destructive due to their Lewis acidic nature, and not long-lasting. The best catalyst system to date is a heterogeneous rhenium catalyst prepared on silica/alumina mixtures (X. Xiaoding and J. C. Mol *J. Chem. Soc. Chem. Comm.* (1985) 631). Maximum activity to date consists of metathesis of about 60 equivalents of methyl oleate to the equilibrium mixture in one hour. Thereafter, the catalyst system is inactive, thereby limiting the practicality of these relatively expensive (Re) catalysts.

It would be desirable to provide a catalyst for metathesizing functionalized olefins at a molecular level that would be based on cheaper metals (Mo, W) and that would be more active and longer lived. Such catalysts can be utilized as homogeneous catalysts or could be attached covalently to inorganic (e.g. silica) or organic (e.g. polystyrene) supports to yield analogous heterogeneous catalysts.

SUMMARY OF THE INVENTION

The compounds of interest have the general formula:

$$M(NR^1)(OR^2)_2(CHR^3) \qquad \text{Formula I}$$

wherein

M is molybdenum or tungsten;

$R^1$ and $R^2$ are alkyl, aryl, aralkyl or halogen-substituted derivatives of silicon-containing analogs thereof;

$R^3$ is an alkyl, aryl, aralkyl or any substituent that results from the initial reaction between the M=$CHR^3$ complex and the olefin(s) that is(are) being metathesized; alkyl has 1–20 carbons, aryl has 6–20 carbons and aralkyl has 7–20 carbons. These compounds are catalysts for the metathesis of ordinary olefins (hydrocarbons) and especially functionalized olefins in the homogeneous phase.

DESCRIPTION OF SPECIFIC EMBODIMENTS

The terms "aryl" and "ar" are employed here to denote a radical derived from a hydrocarbon, having solely aromatic unsaturation in six-membered carbocyclic rings, by removal of a hydrogen atom from a carbon atom of an aromatic ring. Examples of aryl groups are phenyl, 2,6-diisopropylphenyl and 2,4,6-trimethylphenyl. Examples of aralkyl groups are benzyl and triphenylmethyl.

Examples of $R^1$ in Formula I are 2,6-diisopropylphenyl, 2,4,6-trimethylphenyl, 2,6-di-t-butylphenyl, pentafluorophenyl, t-butyl, trimethylsilyl, triphenylmethyl, triphenylsilyl, tri-t-butysilyl, and perfluoro-2-methyl-2-pentyl.

Examples of $R^2$ in Formula I are t-butyl, trifluoro-t-butyl (($CF_3$)($CH_3$)$_2$C), perfluoro-t-butyl, perfluoro-2-methyl-2-pentyl, 2,6-diisopropylphenyl, pentafluorophenyl, trimethylsilyl, triphenylsilyl, tri-t-butylsilyl, and hexafluoro-t-butyl (($CF_3$)$_2$($CH_3$)C).

$R^3$ is initially t-butyl or phenyl, but since the M=$CHR^3$ moiety of the compound of Formula I is intimately involved in the catalytic reaction, the $CHR^3$ ligand is replaced by any other alkylidene fragment from the olefins that are being metathesized.

It is also recognized that one or more donor ligands such as ethers (diethyl ether, tetrahydrofuran, 1,2-dimethoxyethane) can be bound to M in the complex in the crystalline state, but in solution the donor ligands are lost spontaneously, or are displaced readily by the olefin(s) that is(are) being metathesized.

It is also recognized that metallacyclobutane complexes, the simplest of which is

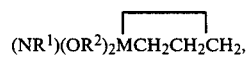

$(NR^1)(OR^2)_2MCH_2CH_2CH_2$, can also be utilized as catalysts for the metathesis reaction, as they are the crucial intermediates in said reaction, and are in equilibrium with the alkylidene complex and the free olefin (e.g., reaction 1).

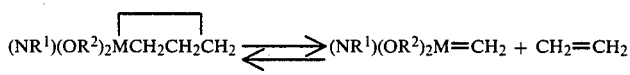

$$(NR^1)(OR^2)_2MCH_2CH_2CH_2 \rightleftharpoons (NR^1)(OR^2)_2M=CH_2 + CH_2=CH_2 \quad (1)$$

The position of the equilibrium in equation 1 will depend upon the donor ability of the solvent medium, and in the more general case where alkyl or functionalized substituents are present in the metallacyclobutane and alkylidene complexes, upon the electronic and steric properties of those substituents.

When $R^3$=t-butyl, the catalyst can be prepared by the sequence of reactions shown in equations 2-4. These reactions can be conducted in diethyl ether, pentane or toluene solvent at a temperature between $-78°$ C. and $25°$ C. The products are recovered by filtering the reaction mixture and removing all solvents and readily volatile products from the filtrate in vacuo.

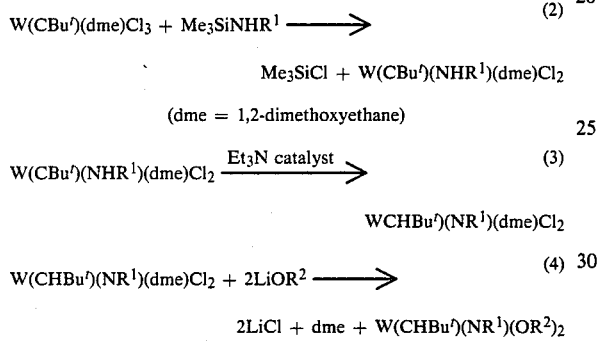

This invention is further illustrated by the following examples, which should not, however, be construed as fully delineating the scope of this discovery.

In order to avoid the presence of oxygen and moisture, the latter being especially destructive, all experiments below were carried out in an atmosphere of dry molecular nitrogen using dry, pure solvents.

W(CBu$^t$)(dimethoxyethane)Cl$_3$ was prepared by the sequence of reactions as described in the literature (R. R. Schrock, et al., *Organometallics* 1 (1982) 1645).

In the examples below Bu$^t$=t-butyl, Me=methyl, Ph=phenyl and Pr$^i$=isopropyl.

While the examples below relate to the preparation and use of tungsten catalysts, it is to be understood that the corresponding molybdenum catalysts can be prepared and used in the same manner.

EXAMPLE I

Preparation of
W(CBu$^t$)(NH—2,6-C$_6$H$_3$Pr$_2^i$)(dimethoxyethane)Cl$_2$

A solution of W(CBu$^t$)(dimethoxyethane)Cl$_3$ (4.0 g, 8.9 mmol) in diethyl ether was cooled to $-20°$ C. and 2.22 g (8.9 mmol) Me$_3$SiNH—2,6—C$_6$H$_3$Pr$_2^i$(trimethylsilyl-2,6-diisopropylphenylamine) in 10 ml of diethyl ether was added. The purple starting material dissolved to give a yellow-orange solution. After 30 min, the solvent was removed in vacuo leaving a bright yellow powder that was recrystallized in the form of yellow cubes from a mixture of pentane and ether at $-40°$ C.; crude yield >95%.

Anal. Calcd for WC$_{21}$H$_{37}$O$_2$Cl$_2$N: C, 42.72; H, 6.27. Found: C, 42.52; H, 6.44. Partial $^1$H NMR (C$_6$D$_6$) $\delta$10.38 (br s, 1, NH), 4.20 (sept, 2, CHMe$_2$), 3.21 (br s, 6, MeOCH$_2$), 3.06 (s, 4, CH$_2$OMe), 1.3 (br s, 6, CHMe$_2$), 1.2 (br s, 6, CHMe$_2$), 0.88 (s, 9, CMe$_3$). Partial $^{13}$C NMR (C$_6$D$_6$) $\delta$304.5 (s, CBu$^t$). IR (Nujol) cm$^{-1}$ 3220 (NH).

EXAMPLE II

Preparation of
W(CHBu$^t$)(N—2,6—C$_6$H$_3$Pr$_2^i$)(dimethoxyethane)Cl$_2$

The crude product of the reaction in Example I was partially dissolved in 100 ml of ether and the mixture was cooled to $-20°$ C. Triethylamine (0.5 $\mu$l) in 3 ml of ether was added to the rapidly stirred mixture. After 1 hour, the volatile components of the new reddish solution were removed in vacuo to give an orange powder of essentially pure W(CHBu$^t$)(N—2,6—C$_6$H$_3$Pr$_2^i$)(dimethoxyethane)Cl$_2$; yield >95%. It can be recrystallized from pentane to give analytically pure orange crystals.

Anal. Calcd for WC$_{21}$H$_{37}$O$_2$Cl$_2$N: C, 42.72; H, 6.27. Found: C, 42.45; H, 6.36. Partial $^1$H NMR (C$_6$D$_6$) $\delta$8.97 (s, 1, CHCMe$_3$, J$_{HW}$=7.3 Hz). Partial $^{13}$C NMR (C$_6$D$_6$) $\delta$283.8 (d, J$_{CH}$=114 Hz, J$_{CW}$=163 Hz).

EXAMPLE III

Preparation of
W(CHBu$^t$)(N—2,6—C$_6$H$_3$Pr$_2^i$)[OCMe(CF$_3$)$_2$]$_2$

The crude product from the reaction in Example II was dissolved in 120 ml of diethyl ether and the solution was cooled to $-20°$ C. LiOCMe(CF$_3$)$_2$ (3.35 g, 17.8 mmol) was added in small portions to the stirred solution. After all of the LiOCMe(CF$_3$)$_2$ had been added, the mixture was warmed to $25°$ C. and filtered through a pad of Celite ®. The solvent was removed from the filtrate in vacuo to give W(CHBu$^t$)(N—2,6—C$_6$H$_3$Pr$_2^i$)[OCMe(CF$_3$)$_2$]$_2$ as a dimethoxyethane adduct. Upon exposing the crude product to a vacuum (1 $\mu$m) for 36 hours, the dimethoxyethane is lost to yield pure W(CHBu$^t$)(N—2,6—C$_6$H$_3$Pr$_2^i$)[OCMe(CF$_3$)$_2$]$_2$; yield $\sim$5.4 g, overall $\sim$75% from W(CBu$^t$)(dimethoxyethane)Cl$_3$.

Anal. Calcd for WC$_{25}$H$_{33}$NO$_2$F$_{12}$: C, 37.93; h, 4.17. Found: C, 37.93, H, 4.34.

EXAMPLE V

Preparation of

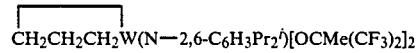

CH$_2$CH$_2$CH$_2$W(N—2,6-C$_6$H$_3$Pr$_2^i$)[OCMe(CF$_3$)$_2$]$_2$

This and several of the following examples illustrate the formation of tungstenacyclobutane intermediates in the reaction of tungsten alkylidene complexes with olefins. A vigorously stirred pentane solution of 0.7 g W(CHBu$^t$)(N—2,6—C$_6$H$_3$Pr$_2^i$)[OCMe(CF$_3$)$_2$]$_2$ cooled to $0°$ C. was treated with 2.4 equivalents of ethylene in a closed system. After 20 minutes, the solvent is removed in vacuo to yield essentially pure light yellow product. It can be recrystallized from a mixture of ether and pentane to give nearly white crystals. The initial metathesis product, t-butylethylene, is formed in 95% yield according to gas chromatographic analysis.

Anal. Calcd for WC$_{39}$H$_{56}$NO$_2$: C, 36.18; H, 3.80. Found: C, 36.24; H, 3.98. Partial $^1$H NMR (C$_6$D$_6$) δ4.66 (m, 2, αCH$_2$), 4.51 (m, 2, αCH$_2$), −0.79 (br t, 1, βCH), −1.39 (br t,1, βCH); $^{13}$C NMR (C$_6$D$_6$) δ100.74 (t, αCH$_2$, J$_{CH}$=158 Hz, J$_{CW}$=67 Hz), −5.10 (t, βCH$_2$, J$_{CH}$=157 Hz).

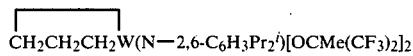

is also a catalyst for the metathesis of olefins (see Example VIII).

EXAMPLE VI

Preparation of

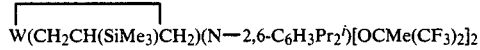

This example illustrates how one tungstenacyclobutane complex can be transformed into another in the presence of an olefin.

Vinyltrimethylsilane (93 μl) was added to a solution of

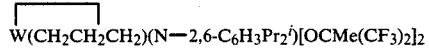

(154 mg) in 10 ml of pentane. After 4 hours, the solvent was removed in vacuo to give essentially pure

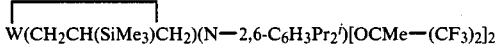

as a yellow oil.

Partial $^1$H NMR (C$_6$D$_6$) δ5.04 (dd, 2, αCH), 4.36 (dd, 2, αCH′), −0.17 (s, 9, SiMe$_3$), −1.03 (tt, 1 βCH).

EXAMPLE VII

Preparation of

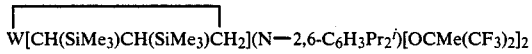

Vinyltrimethylsilane (124 μl) was added to a solution of 212 mg of W(CHBu$^t$)(N—2,6—C$_6$H$_3$Pr$_2^i$)[OCMe(CF$_3$)$_2$]$_2$ in 15 ml of pentane. The solvent was removed in vacuo after two hours to give a light yellow powder that can be recrystallized from pentane as light yellow crystals. The yield of crude product is essentially quantitative.

Partial $^1$H NMR (C$_6$D$_6$) δ5.66 (dd, 1, αCH$_2$), 4.36 (dd, 1, αCH$_2$), 4.04 (m, 1, αCHSiMe$_3$), −0.77 (m, 1, βCHSiMe$_3$).

Single crystal X-ray diffraction showed

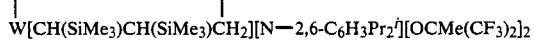

to consist of a distorted trigonal bipyramid with an axial N—2,6—C$_6$H$_3$Pr$_2^i$ group, an equatorial and an axial OCMe(CF$_3$)$_2$ group and the metallacyclic ring located in the equatorial pseudo-plane. The trimethylsilyl substituents are relatively trans to one another on α and β carbon atoms.

EXAMPLE VIII

Metathesis of cis-2-pentene

To 50 mg of W(CHBu$^t$)(N—2,6—C$_6$H$_3$Pr$_2^i$)[OCMe(CF$_3$)$_2$]$_2$ in 5 ml of pentane was added 50 equivalents of cis-2-pentene. After 15 minutes, glc analysis showed a mixture (∼1:1) of the initial metathesis products, 5,5-dimethyl-3-hexene and 4,4-dimethyl-2-pentene, in essentially quantative yield along with an approximately 1:2:1 mixture of 2-butenes, 2-pentenes and 3-hexenes. Sequential addition of a total of 2000 equivalents of cis-2-pentene yielded the expected equilibrium mixture. After 24 hours, the catalyst was still active.

Similar results were obtained employing

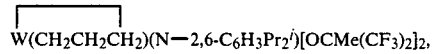

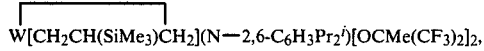

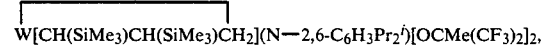

or W(CHBu$^t$)(N—2,6—C$_6$H$_3$Pr$_2^i$)(O—2,6—C$_6$H$_3$Pr$_2^i$)$_2$.

The rate of metathesis employing the 2,6-diisopropylphenoxide catalysts is considerably slower than that employing hexafluoro-t-butoxide catalysts. For example, cis-2-pentene was not metathesized at an appreciable rate at −20° in toluene employing W(CHBu$^t$)-(N—2,6—C$_6$H$_3$Pr$_2^i$)$_2$ while 100 eq of cis-2-pentene was metathesized in 10 minutes by W(CHBu$^t$)(N—2,6—C$_6$H$_3$Pr$_2^i$)[OCMe(CF$_3$)$_2$]$_2$ under the same conditions.

EXAMPLE IX

Metathesis of Methyloleate

W(CHBu$^t$)(N—2,6—C$_6$H$_3$Pr$_2^i$)[OCMe(CF$_3$)$_2$]$_2$ (20 mg, 25.2 μmol) was dissolved in 10 ml of toluene containing a dodecane internal standard. Methyloleate (500 μl, 58 eq) was added. After 30 minutes, the equilibrium (∼1:2:1) between CH$_3$(CH$_2$)$_7$CH=CH(CH$_2$)$_7$CH$_3$, CH$_3$(CH$_2$)$_7$CH=CH(CH$_2$)$_7$CO$_2$Me and MeO$_2$C(CH$_2$)$_7$CH=CH(CH$_2$)$_7$CO$_2$Me was established. Another 600 μl (70 eq) was added. After 1 hour, the equilibrium was reestablished. Both Bu$^t$CH=CH(CH$_2$)$_7$Me and Bu$^t$CH=CH(CH$_2$)$_7$CO$_2$Me, the products of the reaction of the initial catalyst with methyloleate, can be observed in stoichiometric quantities in the reaction mixture. The identity of the initial metathesis products (Bu$^t$CH=CH(CH$_2$)$_7$Me and Bu$^t$CH=CH(CH$_2$)$_7$CO$_2$Me) and the products of catalytic self-metathesis of methyloleate were confirmed by gas chromatography/mass spectroscopy. The activity of this catalyst is at least 250 equivalents of methyl oleate.

Methyloleate is metathesized by

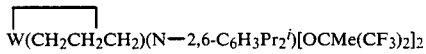

under conditions similar to those above at a rate that is approximately half of the rate noted above employing W(CHBu$^t$)(N—2,6—C$_6$H$_3$Pr$_2^i$)[OCMe(CF$_3$)$_2$]$_2$.

EXAMPLE X

Cross Metathesis of Methyloleate with cis-5-Decene and cis-3-Hexene

W(CHBu$^t$)(N—2,6—C$_6$H$_3$Pr$_2^i$)[OCMe(CF$_3$)$_2$]$_2$ (15 mg, 18.9 μmol) was dissolved in 10 ml of pentane and 20 μl (7.6 eq) of mesitylene (as an internal standard), 707 μl (200 eq) of cis-5-decene, and 400 μl (62.4 eq) of methyloleate were added. After 25 minutes at 25° C., the solution was shown by gas chromatography to contain about 100 eq of 5-decene, about 50 eq each of Me(CH$_2$)$_7$CH=CH(CH$_2$)$_7$Me and Me(CH$_2$)$_3$CH=CH(CH$_2$)$_7$CO$_2$Me along with ~5 eq of Me(CH$_2$)$_7$CH=CH(CH$_2$)$_7$Me, ~10 eq of Me(CH$_2$)$_7$CH=CH(CH$_2$)$_7$CO$_2$Me and ~5 eq of MeO$_2$C(CH$_2$)$_7$CH=CH(CH$_2$)$_7$CO$_2$Me.

A similar experiment employing 29 mg (37 μmol) of W(CHBu$^t$)(N—2,6—C$_6$H$_3$Pr$_2^i$)[OCMe(CF$_3$)$_2$]$_2$, 20 μl (3.93 eq) of mesitylene, 400 μl (89.9 eq) of cis-3-hexene, and 500 μl (32.2 eq) of methyloleate in 10 ml of toluene at 25° C. in ~1 hour yielded a mixture of ~30 eq of 3-hexene, ~15 eq each of MeCH$_2$CH=CH(CH$_2$)$_7$—Me and MeCH$_2$CH=CH(CH$_2$)$_7$CO$_2$Me, and ~1.5 eq of 9-octadecene, ~3 eq of methyloleate and ~1 eq of MeO$_2$C(CH$_2$)$_7$CH=CH(CH$_2$)$_7$CO$_2$Me.

EXAMPLE XI

Preparation of W(CHBu$^t$)(N—2,6—C$_6$H$_3$Pr$_2^i$)(O—2,6—C$_6$H$_3$Pr$_2^i$)$_2$ The crude product from the reaction in Example II was dissolved in 120 ml of ether and the solution was cooled to −20° C. LiO—2,6—C$_6$H$_3$Pr$_2^i$ (3.27 g, 17.8 mmol) was added in small portions to the stirred solution. After all had been added the solution was warmed to 25° C. and filtered through a pad of Celite. The solvent was removed from the filtrate in vacuo to give W(CHBu$^t$)(N—2,6—C$_6$H$_3$Pr$_2^i$)(O—2,6—C$_6$H$_3$Pr$_2^i$)$_2$ in ~75% yield overall based on W(CBu$^t$)(dimethoxyethane)Cl$_3$.

Anal. Calcd for WC$_{41}$H$_{61}$NO$_2$: C, 62.85; H, 6.25. Found: C, 62.68; H, 8.01. Partial $^1$H NMR (C$_6$D$_6$) δ8.41 (s, 1, CHBu$^t$, J$_{HW}$=16 Hz). Partial $^{13}$C NMR (C$_6$D$_6$) 243.4 (CHBu$^t$).

I claim:

1. A catalyst suitable for the metathesis of an olefin having the formula:

M(NR$^1$)(OR$^2$)$_2$(CHR$^3$)

wherein:
R$^1$ and R$^2$ are alkyl, aryl, aralkyl, haloalkyl, haloaryl, haloaralkyl or a silicon-containing analog thereof; and R$^3$ is alkyl, aryl, aralkyl or a substituent resulting from the reaction of the M=CHR$^3$ moiety of said catalyst with an olefin being metathesized and wherein M is Mo or W.

2. A catalyst suitable for the metathesis of an olefin having the formula:

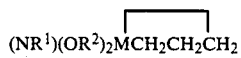

(NR$^1$)(OR$^2$)$_2$MCH$_2$CH$_2$CH$_2$ wherin R$^1$ and R$^2$ are alkyl, aryl, aralkyl, haloalkyl, haloaryl, haloaralkyl or a silicon-containing analog thereof and wherein M is Mo or W.

3. The catalyst of claim 1 wherein R$^3$ is phenyl.

4. The catalyst of claim 1 wherein R$^3$ is t-butyl.

5. The catalyst of anyone of claims 1, 2, 3 or 4 wherein R$^2$ is 2,6-diisopropylphenyl.

6. The catalyst of any one of claims 1, 2, 3 or 4 wherein R$^2$ is 1,1-ditrifluoromethyl ethyl.

7. The catalyst of any one of claims 1, 3 or 4 wherein R$^2$ is 2-trimethylsilyl ethyl cyclobutyl.

* * * * *